(12) United States Patent
Lammel et al.

(10) Patent No.: US 9,103,857 B2
(45) Date of Patent: Aug. 11, 2015

(54) GRADIOMETER FOR DETERMINING THE ELECTRICAL CONDUCTIVITY OF A MEDIUM CONTAINED IN A CONTAINMENT

(75) Inventors: Eric Lammel, Leipzig (DE); Marco Volker, Schwetzingen (DE)

(73) Assignee: ENDRESS + HAUSER CONDUCTA GESELLSCHAFT FUR MESS-UND REGELTECHNIK MBH + CO. KG, Gerlingen (DE)

( * ) Notice: Subject to any disclaimer, the term of this patent is extended or adjusted under 35 U.S.C. 154(b) by 215 days.

(21) Appl. No.: 13/554,220

(22) Filed: Jul. 20, 2012

(65) Prior Publication Data
US 2013/0021042 A1 Jan. 24, 2013

(30) Foreign Application Priority Data
Jul. 21, 2011 (DE) .......................... 10 2011 079 572

(51) Int. Cl.
*G01R 27/22* (2006.01)
*G01N 27/07* (2006.01)

(52) U.S. Cl.
CPC ................ *G01R 27/22* (2013.01); *G01N 27/07* (2013.01)

(58) Field of Classification Search
CPC ........ G01R 27/00; G01R 27/07; G01R 27/22; G01N 27/07
USPC ............ 324/654, 204, 207.15–207.17, 76.75, 324/339, 340, 329, 233, 243, 334
See application file for complete search history.

(56) References Cited

U.S. PATENT DOCUMENTS

| 3,826,973 | A | * | 7/1974 | Pflaum | 324/329 |
|---|---|---|---|---|---|
| 4,792,757 | A | * | 12/1988 | Vail et al. | 324/303 |
| 6,204,667 | B1 | * | 3/2001 | Won | 324/329 |
| 2003/0184299 | A1 | * | 10/2003 | Strack | 324/323 |
| 2004/0149431 | A1 | * | 8/2004 | Wylie et al. | 166/242.1 |
| 2010/0127695 | A1 | * | 5/2010 | Harris | 324/207.16 |

FOREIGN PATENT DOCUMENTS

| CN | 1749781 A | 3/2006 |
|---|---|---|
| DE | 102008047960 A1 | 3/2010 |
| WO | 2011/059499 A1 | 5/2011 |

OTHER PUBLICATIONS

German Search Report in corresponding German Application No. 10 2011 079 572.3, dated May 21, 2012.

* cited by examiner

*Primary Examiner* — Jeff Natalini
(74) *Attorney, Agent, or Firm* — Bacon & Thomas, PLLC

(57) ABSTRACT

A gradiometer for determining electrical conductivity of a medium contained in a containment, comprising: at least a first electrical coil, a second electrical coil and a third electrical coil, wherein the first coil is embodied as a transmitting coil, wherein the second and third coil are embodied as receiving coils; and a holding apparatus. The first, second and third coils are wound on the holding apparatus. The holding apparatus is arranged through a containment opening in a containment wall in such a manner that the first coil is positioned centrally with respect to the containment wall. The second and third coils are arranged mirror symmetrically to the first coil and are inductively coupled with the first coil.

10 Claims, 3 Drawing Sheets

GRADIOMETER FOR DETERMINING THE ELECTRICAL CONDUCTIVITY OF A MEDIUM CONTAINED IN A CONTAINMENT

TECHNICAL FIELD

The invention relates to a gradiometer for determining the electrical conductivity of a medium contained in a containment.

BACKGROUND DISCUSSION

In process measurements technology and in industrial measurements technology, for measurement of the electrical conductivity of a liquid, conductivity sensors are frequently used, which work according to an inductive or a conductive measuring principle.

From EP 990 894 B1, for example, a conductivity sensor is known, which includes at least two electrodes, which, for measurement purposes, are immersed in a medium. For determining the electrical conductivity of the medium, the resistance or conductance of the electrode measuring path in the medium is determined. In the case of known cell constant, the conductivity of the medium can be ascertained therefrom. For measurement of the conductivity of a measured liquid by means of a conductivity sensor, it is absolutely necessary to bring at least two electrodes in contact with the measured liquid.

In the case of the inductive principle of conductivity determination for process media, sensors are applied, which have a transmitting coil, as well as a receiving coil arranged spaced apart from the transmitting coil. Via the transmitting coil, an electromagnetic alternating field is produced, which acts on charged particles—e.g. ions—in the liquid medium, and brings about a corresponding electrical current flow in the medium. Via this electrical current flow, also on the receiving coil, an electromagnetic field arises, which induces a received signal (induction voltage) in the receiving coil according to Faraday's law of induction. This received signal can be evaluated and used for determining the electrical conductivity of the liquid medium.

Typically, inductive conductivity sensors are constructed as follows: The transmitting and receiving coils are, as a rule, embodied as toroidal coils and comprise a traversing opening contactable by the medium, so that the two coils are flowed around by medium. In the case of excitation, the transmitting coil forms a closed electrical current path extending within the medium, which passes through both the transmitting as well as also the receiving coil. By evaluation of the electrical current or voltage signal of the receiving coil in response to the signal of the transmitting coil, the conductivity of the measured liquid can then be ascertained. The principle as such is established in industrial process measurements technology and is documented in a large number of documents in patent literature, for example, in DE 198 51 146 A1.

Gradiometry with the assistance of a gradiometer is the simultaneous measurement of a gradient using two sensors, which are arranged at a fixed distance relative to one another. Frequently, gradiometers are used for measurement of magnetic fields. In such case, the sensors are generally embodied as magnetometers, in the simplest case as coils. In such case, the measured values are most often subtracted one from the other, in order to detect magnetic field differences between the two sensors. Thus, highly precise measurements of the magnetic field can be produced.

Thus, coils in the arrangement can, as gradiometers, be used as conductivity sensors.

Problematic in the case of gradiometers is that, due to the field configuration, they are affected by all conductive objects in their nearer environment. Especially metal objects, e.g. a containment wall, can act in a disturbing manner on the measurement, since eddy currents are generated in them, which bring about a disturbance signal, which is superimposed on the actual measurement signal.

SUMMARY OF THE INVENTION

An object of the invention is to provide a gradiometer for determining electrical conductivity, which is also applicable in the case of metal containments.

The object is achieved by a gradiometer, comprising:
at least a first electrical coil, a second electrical coil and a third electrical coil;
wherein the first coil is embodied as a transmitting coil, wherein the second and third coils are embodied as receiving coils; and
a holding apparatus,
wherein the first, second and third coils are wound on the holding apparatus,
wherein the holding apparatus is arranged through a containment opening in a containment wall in such a manner that the first coil is positioned centrally with respect to containment wall, and
wherein the second and third coils are arranged mirror symmetrically to the first coil and are inductively coupled with the first coil.

Via the central positioning of the first coil with respect to the containment wall and the mirror symmetric arrangement of the second and third coils with respect to the first coil, the advantageous arrangement as gradiometer results, which is advantageous for sensitive measurements of conductivity.

If electrical current, especially alternating electrical current, is sent through the first coil, a magnetic field arises. According to Faraday's law of induction, a voltage is thereby induced in the second and third coils, which, in the case of an ideal, mirror symmetrical arrangement, is equally large in the second and third coils. The electromagnetic waves couple both via the holding apparatus, as well as also via the medium in the containment and the medium outside of the containment. Due to the different electrical properties of the two media, a different voltage is induced in the coil arranged in the containment than in the coil arranged outside of the containment. Typically, a larger voltage is induced in coil arranged the within the containment, since eddy currents are induced in the medium located in the containment via the magnetic field of the first coil. The eddy currents are surrounded by another magnetic field. By determining the difference voltage between the second and third coils, the electrical conductivity of the medium in the containment can be ascertained.

In an advantageous embodiment, the second and third coils are wound in opposite directions. Since, for determining the conductance, the difference between the induced voltages in second and third coils is decisive, and voltages with different signs are induced by the opposite windings of second and third coils, the two voltages need only be added to obtain the difference voltage. Circuit-wise, this is relatively simple to put into practice, and thus is to be viewed as advantageous. Furthermore, the signal of the first coil, which is equally large in the second and third coils, is thus suppressed, so that only the difference voltage is measured. This is likewise advantageous with respect to the circuits, since typically, the signal of the first coil is a good deal larger than the difference signal.

In a preferred embodiment, the second and third coils are electrically interconnected with one another. In such case, both a parallel circuit as well as a serial circuit are options. From an electrical perspective, the second and third coils then indeed form a single circuit; however, physically, they are still composed of two separated winding sections. The ascertaining of the difference voltage is facilitated by this embodiment, and the subsequent circuit complexity is minimized.

In a preferred form of embodiment, a protective layer or a protective system is provided, which is embodied in such a manner that the first, second and third coils are protected from the medium to be examined. Since the medium is frequently chemically and/or biologically aggressive, the coils must be protected against this, in order to enable a lasting operation of the gradiometer.

In an advantageous further development, the holding apparatus is arranged in an electrically non-conductive region of the containment wall. Thus, the gradiometer can be installed in the containment, for example, by means of a flange, and the non-conductive part of the flange is its seal. By installation of the gradiometer in a non-conductive part, undesired eddy currents in the containment wall are prevented, which would deliver a disturbance signal. In the non-conductive part, no eddy currents are generated, and the measurement is thereby more precise and more reproducible. The gradiometer of the invention is thereby especially suitable for metal containments.

In a favorable embodiment, the holding apparatus is arranged with its principal axis perpendicular to the containment wall. Thus, it can ideally be assured that second and third coil have the same separation (in magnitude and angle) from the first coil, and that ideal measuring conditions are present.

In a useful form of embodiment, the holding apparatus is composed of a material with a relative permeability greater than 1. In this form of embodiment, the magnetic field lines are ideally led into the holding apparatus.

In a preferred embodiment, an adjustment system is provided, which is embodied in such a manner that, in the case of the same medium inside and outside of the containment, the voltages induced in the second and third coils are equal at least in terms of magnitude. If, for example, for structural reasons, the case arises, in which the first coil is positioned not exactly centrally with respect to the second and third coils, even in the case of the same media inside and outside of the containment, different voltages are induced in the second and third coils. As a result, a correct determining of the conductance of a medium to be measured also may not be achieved. Via installation of an adjustment system, this situation can also be accounted for, and a difference voltage of 0 V can be achieved in the described state.

In such case, in an advantageous form of embodiment, as an adjustment system, an opening is provided on the end of the holding apparatus facing away from the medium in the containment, wherein this opening is embodied in such a manner that a core with a relative permeability greater than 1 is accommodated therein, and wherein the insertion depth of the core into the opening changes the coupling factor between the first and second and/or first and third coils.

In an alternative form of embodiment, the adjustment system is embodied in the form of at least one superordinated unit. Part of the superordinated unit can be, for example, a microcontroller, which performs the adjustment.

Moreover, the superordinated unit is embodied in such a manner that it generates, open loop controls and/or closed loop controls electrical current, especially alternating electrical current, through the first coil, and/or ascertains and/or further processes the electrical voltages induced in the second and third coils. This can also occur on an individual chip.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
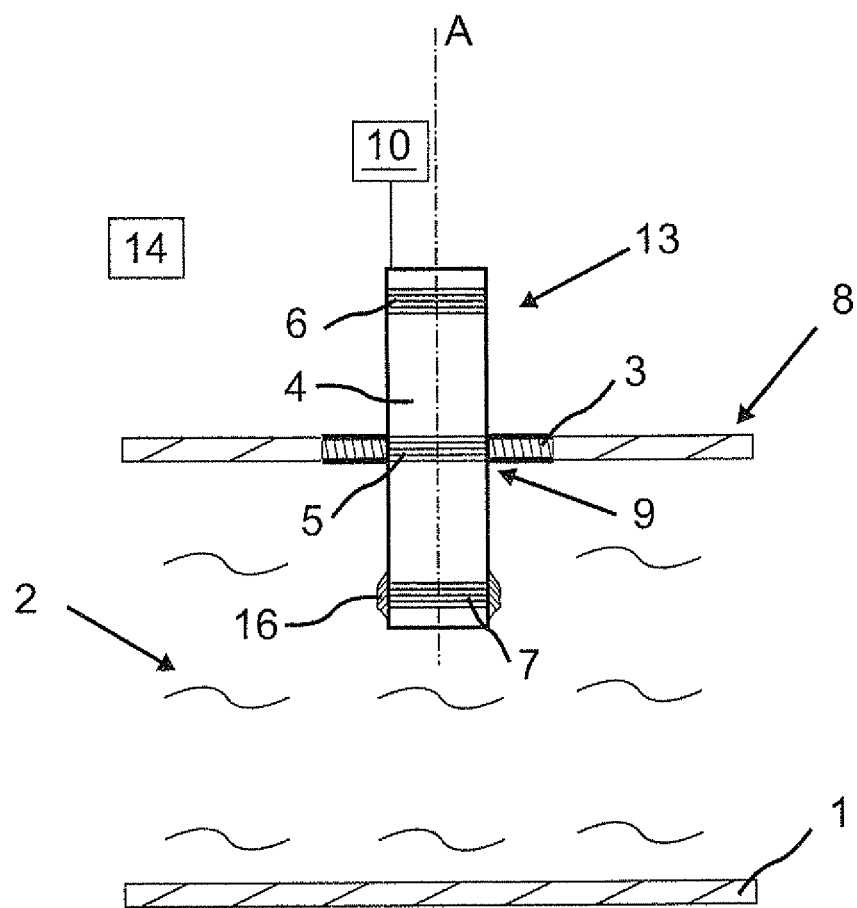
FIG. 1 is a cross section through a containment with a gradiometer.

In the figures, equal features are provided with equal reference characters.

FIG. 1 shows a cross section through a containment 8 containing a liquid medium to be measured 2. Outside of the containment 8, medium 14, typically air, is located. The gradiometer in its totality has the reference character 13. Containment 8 is formed by a containment wall 1, which generally is composed of a metal, for example, aluminum, or a metal alloy, for example, steel. Other forms of embodiment are constructed of non-metallic materials, for example, resistant, synthetic materials, such as polyetheretherketone (PEEK) or polyphenylene sulfone (PPSU).

The gradiometer 13 is arranged in a containment opening 9 in the containment wall 1. Gradiometer 13 is, for example, connected with containment 8 by screwing, adhesive or interlocking. Also implementable are forms of embodiment in the case of which gradiometer 13 is connected with containment 8 via a tubular nozzle with a flange arrangement. Gradiometer 13 can also be part of an assembly, for instance a retractable assembly.

The gradiometer 13 is arranged in an electrically non-conductive region 3 of the containment wall 1. The electrically non-conductive region 3 can be, for example, part of a process connection or flange and be manufactured of PEEK. The electrically non-conductive region 3 can also be a sealing ring and be manufactured of FKM or EPDM.

Gradiometer 13 comprises a holding apparatus 4, which is produced from an electrically non-conductive material, for example, a synthetic material such as PEEK or PPSU. Also implementable are forms of embodiment with metal materials, e.g. made of a ferrite. The holding apparatus 4 can especially be manufactured of a material, which possesses a relative permeability greater than 1.

Holding apparatus 4 typically has a circularly cylindrical shape; however, other embodiments are possible. Usually, the diameter of holding apparatus 4 is the same along its entire length. Holding apparatus 4 can also be embodied as a dowel, plug, bolt, mandrel, web, etc.

Wound on holding apparatus 4 are three coils. In such case, second and third coils 6, 7 are arranged mirror symmetrically to a first coil 5, i.e. the gradiometer is a so-called $2^{nd}$ order gradiometer. The coils are composed of an electrical current conductor, e.g. a wire, lacquered wire or stranded or litz wire. Typically, lacquered copper wire is used. The coils 5, 6, 7 have at least one winding, or turn. The second and third coils 6, 7 most often have equal properties as concerns number of windings, or turns, winding spacing and number of the winding plies. Moreover, the second and third coils 6, 7 are wound in opposite directions and are serially interconnected with one another, wherein also a connection in parallel is possible, or even no connection.

Coils 5, 6, 7 do not contact the medium. Thus, coils 5, 6, 7, can, for example, be embedded in the holding apparatus 4 or be protected from medium 2 by a protective layer 16. The protective layer can be a resistive lacquer, resin, etc.

Figure 2:
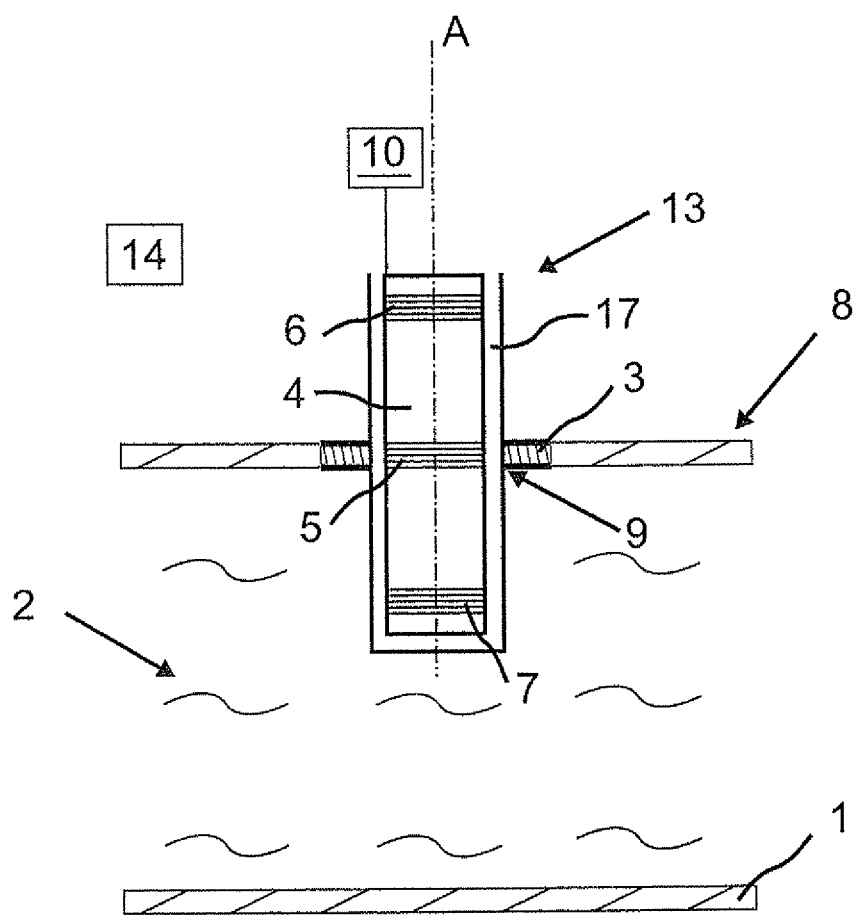
FIG. 2 is a cross section through a containment with a gradiometer and showing an alternative protection for the coils.

FIG. 2 shows an alternative form of embodiment, in the case of which the protection for the coils 5, 6, 7 is composed of a protective system 17. The protective system 17 can be embodied, for example, as a one end open, protective cylinder or tube. The material of protective system 17 must, in such case, be resistant to the medium 2 and is, for example, PEEK or PPSU. Ideally, the material is non-conductive.

First coil 5 is arranged in such a manner that it is positioned centrally in containment wall 1. Typically, the holding apparatus 4 is installed perpendicularly to the containment wall 1; however, other installed angles are also imaginable. Due to the mirror symmetry of the second and third coils 6, 7 to the first coil 5, second and third coils 6, 7 are located spaced equally apart from first coil 5, inside of (second coil 6) or outside of (third coil 7) containment 8.

Coils 5, 6, 7 are connected with a superordinated unit 10. Superordinated unit 10 generates, controls and/or regulates an electrical current, especially an alternating electrical current, which is sent through the first coil 5. In this way, a magnetic field arises in the first coil 5. In such case, superordinated unit 10 is, for example, a circuit for generating and measuring electrical current, and includes, as well, a connected microcontroller. The individual components of the superordinated unit, such as, for example, microcontroller, electrical current generator and electrical current meter, can be composed of only one component.

The electromagnetic waves couple both via the holding apparatus 4 as well as also via the media 2, 14 inside and outside of containment 8. According to Faraday's law of induction, a voltage is then induced in the second and third coils 6, 7, and an electrical current flows in the coils.

Due to the different electrical properties of the media 2, 14 inside and outside of containment 8, in the second coil 6, a different voltage, respectively electrical current, is induced compared to the situation for the third coil 7. Typically, in the third coil 7, i.e. the coil within containment 8, more voltage is induced.

The voltages induced in the second and third coils 6, 7 are further processed in superordinated unit 10, possibly subtracted from one another. By evaluation of the electrical current or voltage signal of the second and third coils 6, 7 in response to the signal of the first coil 5, the electrical conductivity of medium 2 can then be ascertained.

If the medium 2 and the medium 14 located outside of containment 8 possess equal electrical properties, in the case of subtraction of the voltages, a value of 0 V results, when second and third coils 6, 7 are oppositely wound and have equal features such as diameter, winding number, winding spacing and number of winding plies.

The second and third coils 6, 7 can also be electrically interconnected with one another. Thus, either a serial or parallel connection is possible. Second and third coils 6, 7 can be produced from a single-piece electrical current conductor. The coils are then connected in series, but form, however, two physically separated winding sections. The second and third coils 6, 7 are also wound oppositely. In this way, a possible subtraction is omitted, since voltages of different signs are induced, and the voltages can be added with little circuit complexity.

Figure 3:
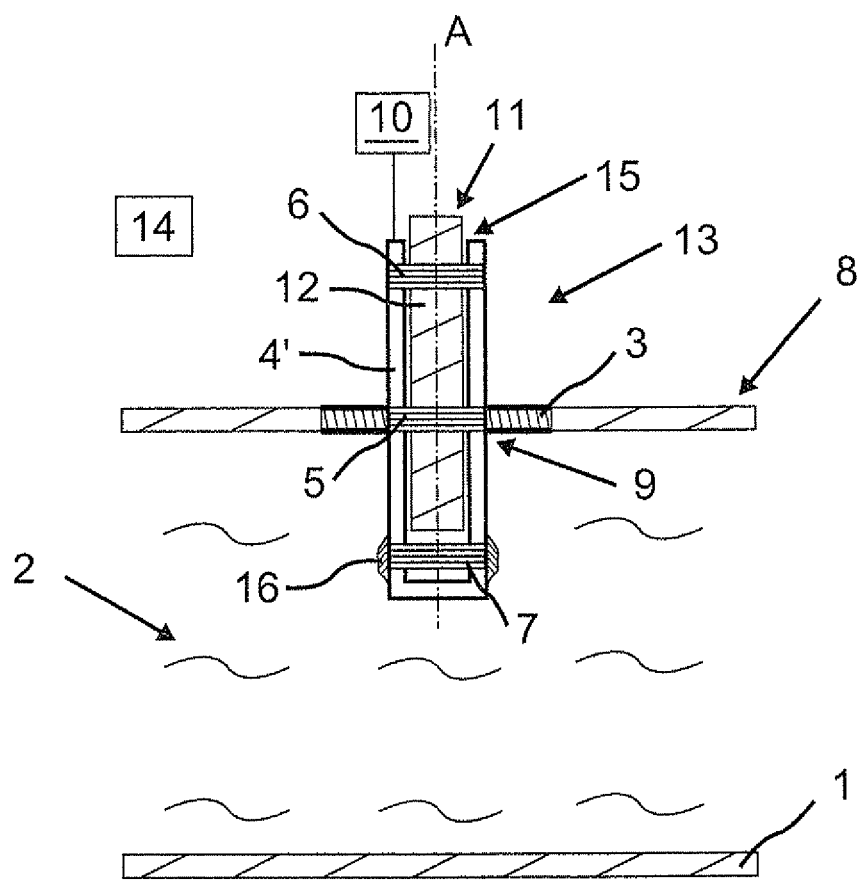
FIG. 3 is a cross section through a containment with a gradiometer, in a second form of embodiment.

FIG. 3 shows another embodiment of the gradiometer 13. As is mentioned above, the first coil 5 is ideally positioned exactly centrally in containment wall 1. In the case of the same media 2, 14 inside and outside of containment 8 and same features of the second and third coils 6, 7, equal voltages are then induced in the second and third coils 6, 7. If the first coil 5 is, however, not positioned exactly centrally in containment wall 1 or second and third coils 6, 7 are positioned at different distances from the first coil 5, different induction voltages are yielded, and the difference voltage is not equal to 0 V. Since this is, however, a prerequisite for a successful determining of the conductance of a medium to be measured, an adjustment must take place.

This can, for example, occur via a corresponding compensation in the superordinated unit 10.

As shown in FIG. 3, gradiometer 13 can, moreover, be provided with an adjustment system 11. In such case, a holding apparatus 4' is, for example, embodied as a one end closed, hollow cylinder, and can typically have the same properties as the holding apparatus 4. Through the opening 15 facing away from the medium 2, a core 12 can be brought into the interior of the holding apparatus 4', wherein the principal axis A of the holding apparatus 4' agrees with the principal axis of the core 12. The core 12 can be produced from a material whose relative permeability is greater than 1. Examples include the ferrites. The coupling factor between first and second coils 5, 6 or between the first and third coils 5, 7 changes as a function of the insertion depth of core 12 into holding apparatus 4'. Thus, the gradiometer 13 can be adjusted in such a manner that, in spite of a non-ideal positioning of the first coil 5 in containment wall 1, the voltages induced in the second and third coils 6, 7 in the case of same media 2, 14 inside and outside of the containment 8 are equal at least in terms of magnitude, and a difference voltage of 0 V results. After the adjusting, the gradiometer can, in the productive use, be used for determining the conductance of a medium 2.

The invention claimed is:

1. A gradiometer for determining electrical conductivity of a first medium contained in a containment,
   wherein the first medium is liquid,
   wherein a second medium is located outside the containment,
   wherein said gradiometer is connected with said containment by screwing, adhesive, interlocking, via a tubular nozzle with a flange arrangement, or as part of a retractable assembly,
   wherein the containment is formed by a containment wall which is composed of a metal or a resistant synthetic material, wherein the containment wall comprises an electrically non-conductive region,
   said gradiometer comprising:
   at least a first electrical coil, a second electrical coil and a third electrical coil, wherein said first coil is embodied as a transmitting coil to transmit electromagnetic waves, and wherein said second and said third coils are embodied as receiving coils; and
   a holding apparatus, wherein:
   said holding apparatus is arranged in said electrically non-conductive region of said containment wall and said holding apparatus is arranged with its principal axis perpendicular to said containment wall;
   said first, said second and said third coils are wound on said holding apparatus;
   said holding apparatus is arranged through a containment opening in a containment wall in such a manner that said first coil is positioned centrally with respect to said containment wall;
   said second and said third coils are arranged mirror symmetrically to said first coil and are inductively coupled with said first coil, and said second coil is arranged outside the first medium and the third coil is arranged in the first medium, wherein said electromagnetic waves couple via the first medium in the containment and the second medium outside the containment wherein a different voltage is induced in the third coil than in the second coil due to different electrical properties of the first and second medium; and the electrical conductivity of said first medium is ascertained based on said different voltage.

2. The gradiometer as claimed in claim 1, wherein:
said second and said third coils are wound in opposite directions.

3. The gradiometer as claimed in claim 1, wherein:
said second and said third coil are electrically interconnected with one another.

4. The gradiometer as claimed in claim 1, further comprising:
a protective layer or a protective system, wherein:
said protective layer or protective system is embodied in such a manner that said first, said second and said third coils are protected from the medium.

5. The gradiometer as claimed in claim 1, wherein:
said holding apparatus is composed of a material with a relative permeability greater than 1.

6. The gradiometer as claimed in claim 1, further comprising:
an adjustment system, which is embodied in such a manner that, in the case of the same medium inside and outside of said containment, the voltages induced in said second and said third coils are equal at least in terms of magnitude.

7. The gradiometer as claimed in claim 6, wherein:
as said adjustment system, an opening is provided on the end of said holding apparatus facing away from the medium;
said opening is embodied in such a manner that a core with a relative permeability greater than 1 is accommodated therein; and
the insertion depth of said core into said opening changes the coupling factor between said first and said second coils and/or said first and said third coils.

8. The gradiometer as claimed in claim 6, wherein:
said adjustment system is embodied in the form of at least one superordinated unit and performs the adjustment of the voltages induced in said second and said third coils.

9. The gradiometer as claimed in claim 1, further comprising:
at least one superordinated unit, which is embodied in such a manner that it generates, open loop controls and/or closed loop controls electrical current, especially alternating electrical current, through said first coil; and/or ascertains and/or further processes the electrical voltages induced in said second and said third coils.

10. The gradiometer as claimed in claim 1, wherein
a larger voltage is induced in the third coil than in the second coil.

* * * * *